US012751753B1

(12) United States Patent
Antonacci et al.

(10) Patent No.: US 12,751,753 B1
(45) Date of Patent: Oct. 6, 2026

(54) CLOSED CHANNEL ANCHOR DEVICE FOR BONE IMPLANTATION DURING SURGICAL PROCEDURES

(71) Applicants: M Darryl Antonacci, Skillman, NJ (US); Matthew L Cavuto, London (GB); Anthony C Antonacci, Ridgefield, CT (US)

(72) Inventors: M Darryl Antonacci, Skillman, NJ (US); Matthew L Cavuto, London (GB); Anthony C Antonacci, Ridgefield, CT (US)

(73) Assignee: Caliber CLA Holdings LLC, Sheridan, WY (US)

( * ) Notice: Subject to any disclaimer, the term of this patent is extended or adjusted under 35 U.S.C. 154(b) by 0 days.

(21) Appl. No.: 19/290,760

(22) Filed: Aug. 5, 2025

(51) Int. Cl.
*A61B 17/70* (2006.01)
*A61B 17/88* (2006.01)

(52) U.S. Cl.
CPC ...... *A61B 17/8869* (2013.01); *A61B 17/7032* (2013.01)

(58) Field of Classification Search
CPC ............ A61B 17/7032; A61B 17/7022; A61B 17/705; A61B 17/7001
See application file for complete search history.

(56) References Cited

U.S. PATENT DOCUMENTS 2,464,432 A * 3/1949 Brickman ............... B21F 27/08 140/9
5,415,658 A * 5/1995 Kilpela ................ A61B 17/842 606/300
5,496,321 A * 3/1996 Puno .................. A61B 17/7091 606/305
5,545,164 A 8/1996 Howland
5,584,831 A 12/1996 McKay
5,601,554 A * 2/1997 Howland ........... A61B 17/7049 606/252
5,662,653 A 9/1997 Songer et al.
6,053,921 A * 4/2000 Wagner ............. A61B 17/8869 606/103
6,251,112 B1 6/2001 Jackson
6,478,798 B1 11/2002 Howland
6,520,965 B2 * 2/2003 Chervitz .............. A61B 17/842 606/103
6,793,657 B2 9/2004 Lee et al.
(Continued)

FOREIGN PATENT DOCUMENTS

KR 20240068262 A * 5/2024 ........... A61B 17/842

*Primary Examiner* — Jacqueline T Johanas
(74) *Attorney, Agent, or Firm* — Sutton Magidoff Barkume LLP

(57) ABSTRACT

A closed channel anchor device for insertion into a bone having a post and a cord housing coupled to the post, a first dual channel embodiment having a pair of cord channels extending therethrough and a cavity open from a top surface of the housing having a socket having socket threads for receiving a threaded fastener and a pair of socket apertures each opening into a cord channel. When a cord is inserted through each cord channel and a threaded fastener is threaded into the socket, the threaded fastener protrudes into each socket aperture to at least partially compress each cord to hold each cord within their respective cord channel. A second embodiment with a single cord channel is also provided.

24 Claims, 16 Drawing Sheets

(56) References Cited

U.S. PATENT DOCUMENTS

| | | | | |
|---|---|---|---|---|
| 6,960,213 | B2 * | 11/2005 | Chervitz | A61B 17/82 606/103 |
| 7,166,109 | B2 | 1/2007 | Biedermann et al. | |
| 7,806,912 | B2 * | 10/2010 | Lawton | A61B 17/7049 606/260 |
| 7,819,899 | B2 | 10/2010 | Lancial | |
| 7,922,748 | B2 | 4/2011 | Hoffman | |
| 8,034,085 | B2 * | 10/2011 | Slivka | A61B 17/7044 606/270 |
| 8,052,720 | B2 | 11/2011 | Kuester et al. | |
| 8,142,434 | B2 * | 3/2012 | Bluechel | F16G 11/101 606/280 |
| 8,177,810 | B2 * | 5/2012 | Ferree | A61B 17/8861 606/264 |
| 8,246,657 | B1 * | 8/2012 | Samuel | A61B 17/7049 606/250 |
| 8,641,736 | B2 * | 2/2014 | Marik | A61B 17/7022 606/254 |
| 8,992,579 | B1 | 3/2015 | Gustine et al. | |
| 9,339,307 | B2 * | 5/2016 | McClintock | A61B 17/7041 |
| 9,345,517 | B2 | 5/2016 | Zhang et al. | |
| 9,463,048 | B2 | 10/2016 | Iott et al. | |
| 9,526,526 | B2 | 12/2016 | Zhang et al. | |
| 9,532,810 | B2 | 1/2017 | Hestad et al. | |
| 9,962,195 | B2 * | 5/2018 | Larroque-Lahitette | A61B 17/7053 |
| 10,278,736 | B2 | 5/2019 | Samdani et al. | |
| 11,464,547 | B2 | 10/2022 | Biyani et al. | |
| 11,547,452 | B2 * | 1/2023 | Antonacci | A61B 6/505 |
| 11,653,955 | B2 * | 5/2023 | Biedermann | A61B 17/7025 606/252 |
| 11,684,394 | B2 * | 6/2023 | Nichols | A61B 17/7004 606/270 |
| 12,232,777 | B2 * | 2/2025 | Belliard | A61B 17/7002 |
| 12,343,055 | B1 * | 7/2025 | Antonacci | A61B 17/846 |
| 2005/0059972 | A1 * | 3/2005 | Biscup | A61B 17/7061 606/907 |
| 2005/0240180 | A1 | 10/2005 | Vienney et al. | |
| 2005/0277920 | A1 * | 12/2005 | Slivka | A61B 17/7044 606/279 |
| 2006/0064090 | A1 | 3/2006 | Park | |
| 2006/0069390 | A1 | 3/2006 | Frigg et al. | |
| 2006/0089644 | A1 | 4/2006 | Felix | |
| 2006/0206114 | A1 * | 9/2006 | Ensign | A61B 17/7052 606/279 |
| 2006/0233597 | A1 * | 10/2006 | Ensign | A61B 17/7037 403/177 |
| 2007/0123860 | A1 * | 5/2007 | Francis | A61B 17/7044 606/250 |
| 2007/0161994 | A1 | 7/2007 | Lowery et al. | |
| 2007/0191844 | A1 * | 8/2007 | Carls | A61B 17/705 606/86 A |
| 2007/0225708 | A1 | 9/2007 | Biedermann et al. | |
| 2008/0009863 | A1 | 1/2008 | Bond et al. | |
| 2008/0051788 | A1 * | 2/2008 | Schwab | A61B 17/7001 606/279 |
| 2009/0088799 | A1 * | 4/2009 | Yeh | A61B 17/7083 606/264 |
| 2009/0198273 | A1 * | 8/2009 | Zhang | A61B 17/8685 606/264 |
| 2010/0057125 | A1 * | 3/2010 | Viker | A61B 17/7005 606/264 |
| 2010/0063551 | A1 * | 3/2010 | Richelsoph | A61B 17/7026 606/301 |
| 2010/0087861 | A1 | 4/2010 | Lechmann et al. | |
| 2010/0331884 | A1 * | 12/2010 | Hestad | A61B 17/7022 606/279 |
| 2011/0009906 | A1 * | 1/2011 | Hestad | A61B 17/7022 606/264 |
| 2011/0106179 | A1 | 5/2011 | Prevost et al. | |
| 2011/0208254 | A1 | 8/2011 | Villa et al. | |
| 2011/0270314 | A1 | 11/2011 | Mueller et al. | |
| 2012/0029566 | A1 | 2/2012 | Rezach | |
| 2012/0029567 | A1 * | 2/2012 | Zolotov | A61B 17/705 606/264 |
| 2012/0029568 | A1 * | 2/2012 | Jackson | A61B 17/702 606/264 |
| 2013/0079833 | A1 | 3/2013 | Biedermann | |
| 2013/0274808 | A1 | 10/2013 | Larroque-Lahitette et al. | |
| 2014/0303674 | A1 * | 10/2014 | Sasing | A61B 17/705 606/279 |
| 2015/0045836 | A1 * | 2/2015 | Leuenberger | A61B 17/8047 606/281 |
| 2015/0119945 | A1 | 4/2015 | Sasing | |
| 2015/0359568 | A1 * | 12/2015 | Rezach | A61B 17/7032 606/266 |
| 2016/0354118 | A1 * | 12/2016 | Belliard | A61B 17/7053 |
| 2017/0281237 | A1 * | 10/2017 | Murray | A61B 17/7004 |
| 2018/0064469 | A1 * | 3/2018 | Blakemore | A61B 17/7022 |
| 2019/0029734 | A1 * | 1/2019 | Mickiewicz | A61B 17/7053 |
| 2019/0175223 | A1 * | 6/2019 | Nguyen | A61B 17/8605 |
| 2019/0192190 | A1 * | 6/2019 | Gray | A61B 17/7034 |
| 2019/0290334 | A1 * | 9/2019 | Prygoski | A61B 17/809 |
| 2019/0298420 | A1 | 10/2019 | Mishra et al. | |
| 2020/0078051 | A1 | 3/2020 | Faulhaber | |
| 2020/0085471 | A1 * | 3/2020 | McClintock | A61B 17/8625 |
| 2020/0170696 | A1 * | 6/2020 | Haber | A61B 17/7044 |
| 2020/0297389 | A1 | 9/2020 | Shluzas et al. | |
| 2020/0323562 | A1 * | 10/2020 | Hoernschemeyer | A61B 17/7044 |
| 2021/0322060 | A1 * | 10/2021 | Barrett | A61B 17/7016 |
| 2022/0110662 | A1 * | 4/2022 | LaColla | A61B 17/7044 |
| 2022/0117636 | A1 * | 4/2022 | Murray | A61B 17/7022 |
| 2022/0226023 | A1 * | 7/2022 | Mast | A61B 17/7041 |
| 2023/0190336 | A1 | 6/2023 | Leff et al. | |
| 2023/0310037 | A1 | 10/2023 | Glerum et al. | |
| 2024/0164814 | A1 | 5/2024 | Redmond et al. | |
| 2024/0307095 | A1 | 9/2024 | Bales | |
| 2024/0315738 | A1 * | 9/2024 | Baccelli | A61B 17/7053 |

* cited by examiner

CLOSED CHANNEL ANCHOR DEVICE FOR BONE IMPLANTATION DURING SURGICAL PROCEDURES

TECHNICAL FIELD

This application relates to improved anchor devices for implantation into a bone such as a vertebra during spinal correction surgery, such as for the correction of scoliosis using non fusion or modified fusion anterior scoliosis correction, and for other spinal abnormalities.

BACKGROUND OF THE INVENTION

Recent developments in scoliosis treatment, referred to generally as vertebral body tethering (VBT), is a non-fusion surgery that has been found to provide advantages over bracing and fusion techniques of the prior art. In particular, recent advances have been made in de-rotation procedures, as taught in U.S. Pat. No. 11,547,452 METHOD FOR IMPROVED SPINAL CORRECTION SURGERY IMPLEMENTING NON-FUSION ANTERIOR SCOLIOSIS CORRECTION TECHNIQUES WITH VERTEBRAE DE-ROTATION. As explained in the '452 patent, which is incorporated by reference herein, a plurality of anchor devices are inserted onto various vertebral bodies of the patient, via a mini-opening in the patient and/or a portal. Each anchor device has a channel disposed therein, such that a cord or tether may be placed into the channels. One end of the tether is secured within a corresponding anchor device.

Then, a de-rotation vertebrae adjustment procedure is performed, as explained in the '452 patent. After this de-rotation maneuver is performed, then the cord is tensioned in the channel of a second anchor screw, and the tensioned cord is secured in the channel of the second anchor screw in order to maintain the de-rotation.

Thus, the cord is tensioned so as to urge the other channels in which the cord is disposed, along with the corresponding vertebral bodies, towards a straighter orientation. The cord is secured in all the channels using a tensioner, thus urging the spine towards correction of the scoliosis condition with de-rotation and compression or other dimensionality. Optionally, the cord may be adjusted during a subsequent follow-up procedure so as to continue to correct the scoliosis condition over a greater period of time. This is particularly beneficial to younger patients whose spine is still growing. The patient often can leave the hospital within a few days of the surgery and may be able to return to normal activities, including athletic activities, within six weeks or so.

The anchor devices required for this anterior scoliosis correction and other VBT procedures that are available in the prior art suffer from several disadvantages. These anchor devices were initially designed to be used with rigid metal rods, rather than a flexible cord/tether as is now done in modern anterior scoliosis correction and/or VBT procedures, and they have been found to cause wearing and eventual breakage in the flexible cords as they tend to rub against the anchor device due to being urged in a non-linear manner along the deformed spine. Another problem in current anchor devices is the manner in which the cord is held in place after being tightened; again, due to the design for use with a rigid rod rather than a flexible cord, which also causes premature wear and tear. The current anchor devices are also bulky and rough edged due to design adaptations from rigid metal rod concepts and are known to potentially cause local tissue erosion in select cases as well as cord breakage. In addition, modern anterior scoliosis correction techniques incorporate non-fusion and modified fusion principles and may utilize multiple cords (two or more), thus necessitating use of additional anchor devices in the patient's spine in order to support the multiple cords (see the '452 patent) that may not have enough bone mass to provide adequate support.

These problems are addressed by the anchor devices of the present invention as will now be described.

SUMMARY OF THE INVENTION

Provided herein are several embodiments for an anchor device for insertion into a bone. In a first embodiment, a dual channel anchor device is provided to utilize a pair of tensioning cords, which is useful in certain situations in order to provide more precise adjustment of the spine.

In this first embodiment, the dual channel anchor device has a post suitable for implantation into a bone, and a cord housing coupled to the post. The cord housing includes a pair of cord channels having a first cord channel extending through the housing and a second cord channel extending through the housing. A cavity is open from a top surface of the housing, preferably located between the pair of cord channels. The cavity has a socket (e.g. substantially cylindrical) extending into the housing, the socket having socket threads for receiving a threaded fastener, a first socket aperture opening into the first cord channel, and a second socket aperture opening into the second cord channel.

A threaded fastener having threads mated to the socket threads is also provided. As such, when a first cord is inserted through the first cord channel and a second cord is inserted through the second cord channel, and the threaded fastener is threaded into the socket, the threaded fastener protrudes into the first socket aperture to at least partially compress the first cord and into the second socket aperture to at least partially compress the second cord and to hold each of the cords within their respective cord channel.

Optionally, the threads of the threaded fastener have sharp crested threads near a tip of the fastener, rounded crested threads in a middle portion of the fastener, and sharp crested threads near a head of the fastener.

The socket may terminate with a stop against which the threaded fastener is tightened to hold each of the cords within their respective cord channel. The threaded fastener may optionally include means for biasing the threaded fastener within the socket in order to hold it in place after tightening. The means for biasing the threaded fastener within the socket may, for example, be a ball nose spring plunger comprising a biasing spring within a channel of the fastener adjacent a ball at a distal end of the fastener, whereby, when the threaded fastener is tightened so that the ball is urged against the stop, the biasing spring is compressed so as to impart a force in the opposite direction and secure the threaded fastener within the socket.

Preferably, the socket of the anchor device is disposed at an acute angle with respect to the top surface of the housing, for example a 45-degree angle.

Optionally, each cord channel of the anchor device may have a first end portion, a middle portion, and a second end portion, wherein the first end portion and the second end portion have surfaces that are outwardly flared, whereby the outwardly flared surfaces enable the cord to bend and flex where the cord enters and exits the cord channel without undue wear on the cord (i.e., any potential wear will be minimized).

Further optionally, the middle portion of each cord channel may have a non-smooth surface suitable for gripping the cord when inserted therewithin, for example a plurality of ribs extending substantially perpendicular to the direction in which the cord is placed within the channel. As such, a locally compressive force is imparted on the cord so that the cord is held securely in place when a threaded fastener is threaded into the socket, and the cord is prevented from being pulled in either direction in the event there are forces on the cord imparted during use.

In addition, the non-smooth surface of each cord channel may have a void, whereby a locally compressive force is imparted on a cord placed within the channel so that the cord at least partially deflects into the void and is held securely in place when a threaded fastener is threaded into the socket, and the cord is prevented from being pulled in either direction in the event there are forces on the cord imparted during use. Alternatively, the non-smooth surface of each cord channel may have a protrusion, whereby a locally compressive force is imparted on a cord placed within the channel so that the cord is held securely in place when a threaded fastener is threaded into the socket, and the cord is prevented from being pulled in either direction in the event there are forces on the cord imparted during use.

Although the dual channel anchor device of the first embodiment may also be used with a single cord in either cord channel if desired, also provided herein is a second embodiment that includes a single cord channel for situations where only a single cord is needed.

In this second embodiment, the single channel anchor device has a post suitable for implantation into a bone, and a cord housing coupled to the post. The cord housing includes a cord channel extending through the housing; the cord channel preferably located over the post. A cavity is open from a top surface of the housing, the cavity located adjacent the cord channel. The cavity has a socket (e.g., substantially cylindrical) extending into the housing, the socket having socket threads for receiving a threaded fastener and a socket aperture opening into the cord channel.

A threaded fastener having threads mated to the socket threads is also provided. As such, when a cord is inserted through the cord channel and the threaded fastener is threaded into the socket, the threaded fastener protrudes into the socket aperture to at least partially compress the cord and to hold the cord within the cord channel.

Optionally, the threads of the threaded fastener have sharp crested threads near a tip of the fastener, rounded crested threads in a middle portion of the fastener, and sharp crested threads near a head of the fastener.

The socket may terminate at a stop against which the threaded fastener is tightened to hold the cord within the cord channel. The threaded fastener may optionally include means for biasing the threaded fastener within the socket in order to hold it in place after tightening. The means for biasing the threaded fastener within the socket may, for example, be a ball nose spring plunger comprising a biasing spring within a channel of the fastener adjacent a ball at a distal end of the fastener, whereby, when the threaded fastener is tightened so that the ball is urged against the stop, the biasing spring is compressed so as to impart a force in the opposite direction and secure the threaded fastener within the socket.

Preferably, the socket of the anchor device is disposed at an acute angle with respect to the top surface of the housing, for example a 45-degree angle.

Optionally, the cord channel of the anchor device may have a first end portion, a middle portion, and a second end portion, wherein the first end portion and the second end portion have surfaces that are outwardly flared, whereby the outwardly flared surfaces enable the cord to bend and flex where the cord enters and exits the cord channel without undue wear on the cord (i.e., any potential wear will be minimized).

Further optionally, the middle portion of the cord channel may have a non-smooth surface suitable for gripping the cord when inserted therewithin, for example a plurality of ribs extending substantially perpendicular to the direction in which the cord is placed within the channel. As such, a locally compressive force is imparted on the cord so that the cord is held securely in place when a threaded fastener is threaded into the socket, and the cord is prevented from being pulled in either direction in the event there are forces on the cord imparted during use.

In addition, the non-smooth surface of the cord channel may have a void, whereby a locally compressive force is imparted on a cord placed within the channel so that the cord at least partially deflects into the void and is held securely in place when a threaded fastener is threaded into the socket, and the cord is prevented from being pulled in either direction in the event there are forces on the cord imparted during use. Alternatively, the non-smooth surface of the cord channel may have a protrusion, whereby a locally compressive force is imparted on a cord placed within the channel so that the cord is held securely in place when a threaded fastener is threaded into the socket, and the cord is prevented from being pulled in either direction in the event there are forces on the cord imparted during use.

DETAILED DESCRIPTION OF THE INVENTION

The present invention is an improved anchor device, useful for example in surgical techniques wherein the anchor device is inserted into a bone of a patient during scoliosis correction surgery and the like. As explained above, an anchor device is inserted into each of several vertebrae, through which a device such as a tether, cord or band is inserted and secured to enable the surgeon to impart various forces along the spine in an effort to correct for scoliosis or kyphosis. It is noted that when the term "cord" is used herein, it is intended to include other types of flexible devices such as straps, tethers, bands, cables and the like.

Figure 10:
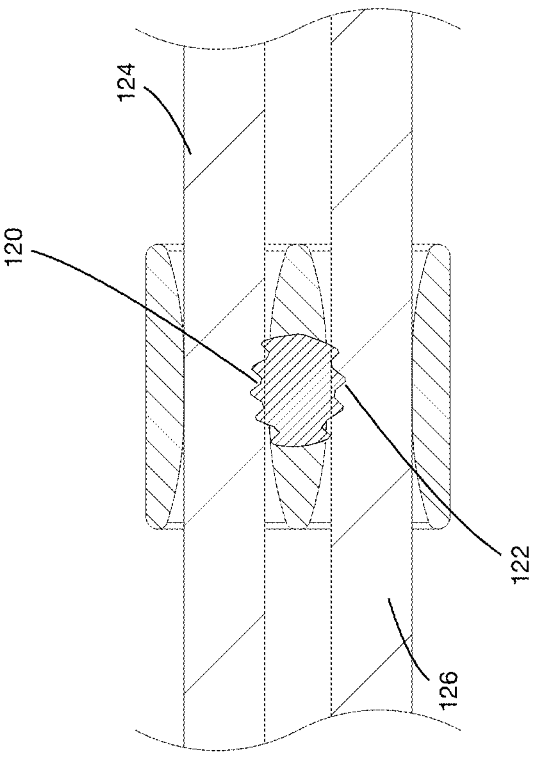
FIG. 10 is a cross-section of the top view of the first embodiment of FIG. 1.
Figure 12:
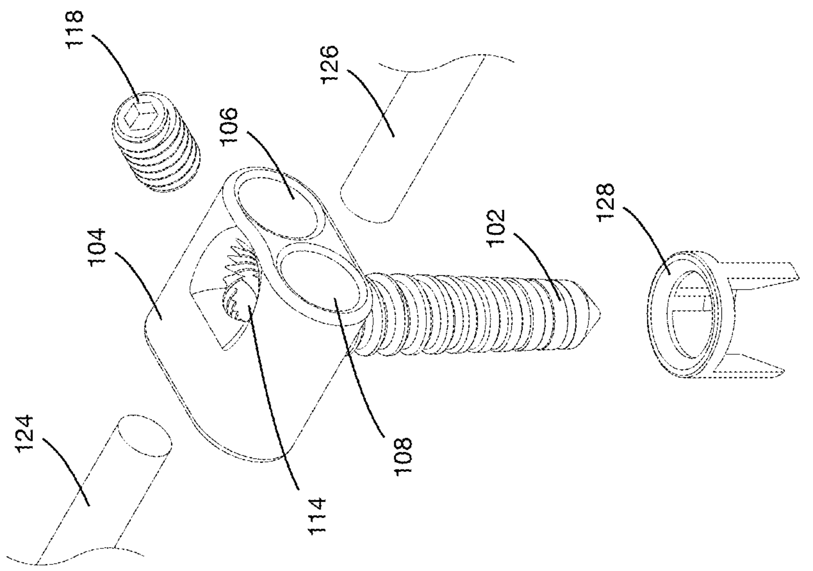
FIG. 12 is an exploded perspective view of the first embodiment of FIG. 1 with a staple for insertion onto the bone.
Figure 11:
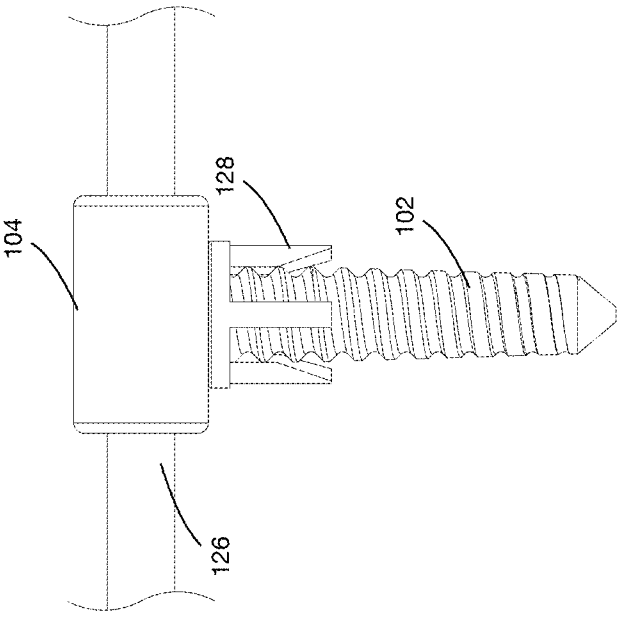
FIG. 11 is an illustration of the first embodiment of FIG. 1 with a staple for insertion onto the bone.
Figure 14:
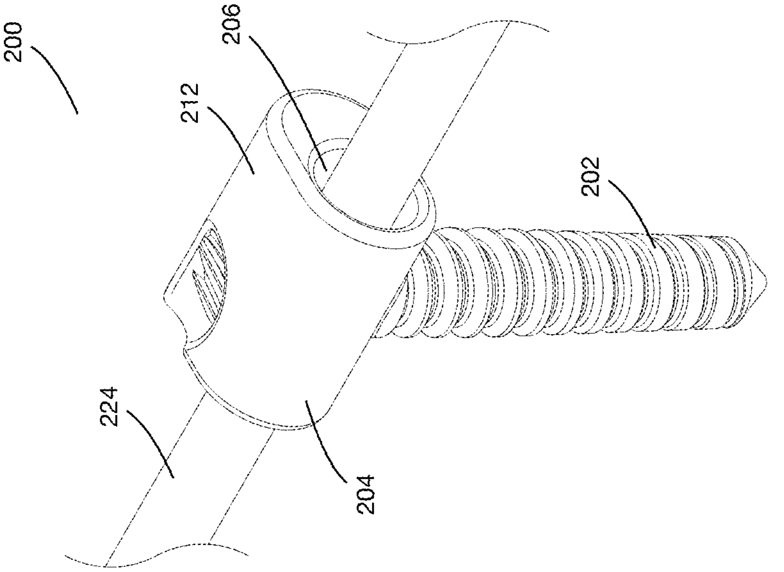
FIG. 14 is a top rear perspective view of the second embodiment of FIG. 13.
Figure 13:
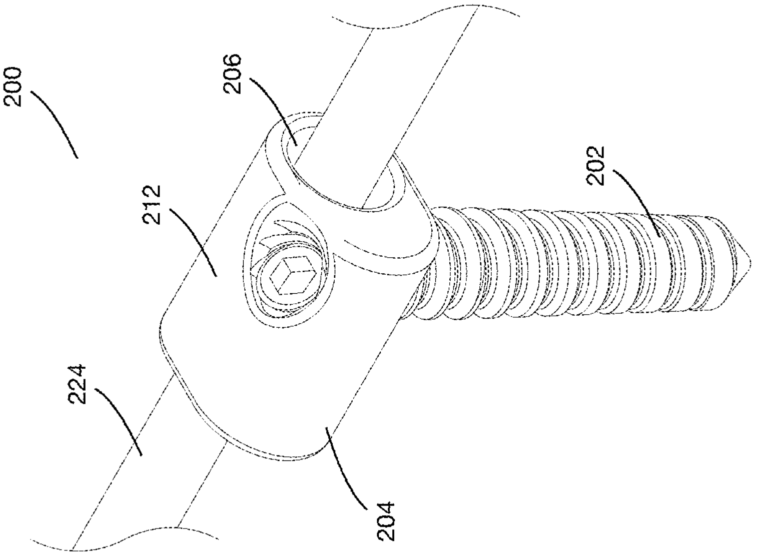
FIG. 13 is a top front perspective view of a second embodiment of the invention in which a single cord channel is provided.
Figure 15:
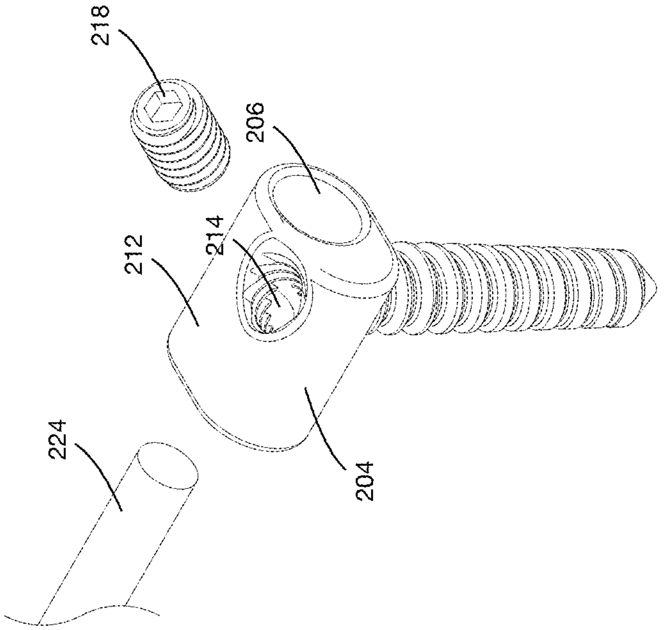
FIG. 15 is an exploded view of the second embodiment of FIG. 13.

With reference to FIGS. 1-12, the first embodiment of the anchor device, which is a dual channel anchor device suitable for implementation with a pair of cords, is shown. The dual channel anchor device 100 includes a threaded post 102 suitable for implantation into a bone as known in the art, and a cord housing 104 that is coupled to the post. The cord housing 104 may be fixedly coupled to the post 102 as shown, so that the connection is rigid and unmoving, or the cord housing may be rotatably or otherwise movably coupled to the post. Shown in FIGS. 11 and 12 is a bone anchoring staple 128, as well known in the art, that may be utilized with the dual channel and single channel anchor devices of the present invention.

In this first embodiment, the cord housing 104 of the dual channel anchor device 100 includes a pair of cord channels, i.e., a first cord channel 106 and a second cord channel 108, both of which extend through the cord housing 104. The cord channels 106, 108 are closed loops and allow insertion therethrough of a first tensioning cord 124 and a second tensioning cord 126 as shown. A cavity 110 is open from a top surface 112 of the cord housing 104, and is preferably located between the pair of cord channels 106, 108. The cavity 110 has a socket 114 (see FIGS. 3 and 12) extending into the housing 104. Preferably, the socket 114 is substantially cylindrical and has socket threads 116 for receiving a threaded fastener 118, which is used to hold the cords 124, 126 in place within the channels 106, 108 after being tensioned by the surgeon. Note that the cords 124, 126 may be inserted or threaded into the cord housing 104 from either direction as may be desired by the surgeon.

Figure 7:
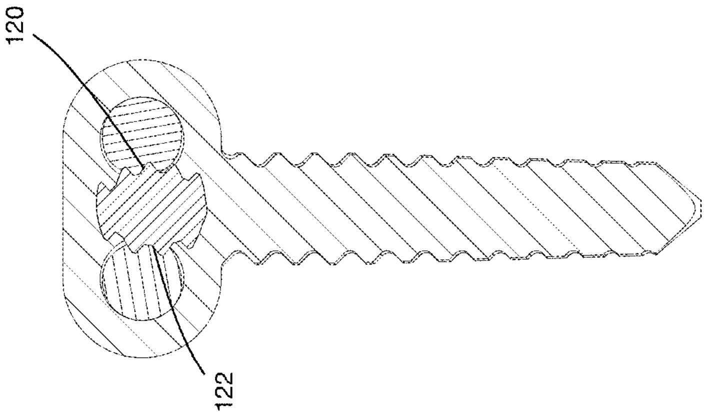
FIG. 7 is a cross-section front view of the first embodiment of FIG. 1.
Figure 6:
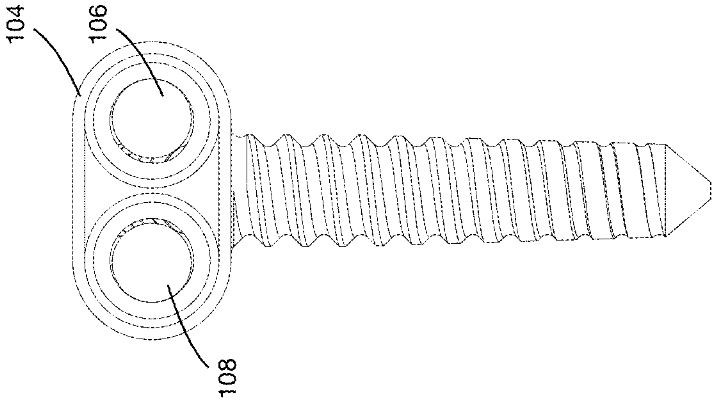
FIG. 6 is a front view of the first embodiment of FIG. 1.

Reference is now made to FIGS. 7 and 10, which show a first socket aperture 120 opening into the first cord channel 106, and a second socket aperture 122 opening into the second cord channel 108. Each socket aperture 120, 122 are essentially openings in the wall of the socket 114 that lead into the cord channels 106, 108. This allows the mating threads of the threaded fastener 118 to enter into the space in each channel 106, 108 and grab each cord 124, 126 that has been inserted therethrough. As the threaded fastener is tightened into the socket 114, the threads of the fastener 118 press against the cord 124, 126 in order to secure each cord within their respective channel 106, 108. See also FIG. 9.

As such, when the first cord 124 is inserted through the first cord channel 106 and the second cord 126 is inserted through the second cord channel 108, and the threaded fastener 118 is threaded into the socket 114, the threaded fastener 118 protrudes into the first socket aperture 120 to at least partially compress the first cord 124 and into the second socket aperture 122 to at least partially compress the second cord 126 and to hold each of the cords within their respective cord channel.

It is noted that in the prior art, it is the tip of the fastener (such as a set screw) which impinges directly upon the cord in place within the corresponding anchor device. However, this invention does not rely on the tip of the fastener 118 to secure the cord in place, i.e. the tip of the fastener does not impinge directly on and impart direct force upon the cord. Instead, the fastener 118 is threaded within the socket threads 116 of the socket 114 such that the threads of the fastener 118 enter into the space in each channel 106, 108 and grab each cord 124, 126 that has been inserted therethrough.

As shown, in the preferred embodiments, the head of the fastener 118 is countersunk within the cavity 110 of the housing 104, although this is not required. The head of the fastener 118 is shown with a hex profile, but others may be used, such as square, slotted, Phillips, etc. This avoids the problem in the prior art described above wherein the force of the tip of the set screw directly onto the cord will deleteriously pinch the cord, which can lead to undesired fraying or other damage to the cord.

Optionally, the threads of the threaded fastener have sharp crested threads near a tip of the fastener, rounded crested threads in a middle portion of the fastener, and sharp crested threads near a head of the fastener. By implementing rounded crested threads rather than sharp crested threads in the middle portion of the fastener, the cord will not be undesirably cut by the threads of the fastener as the hold the cord securely in place.

Figure 2:
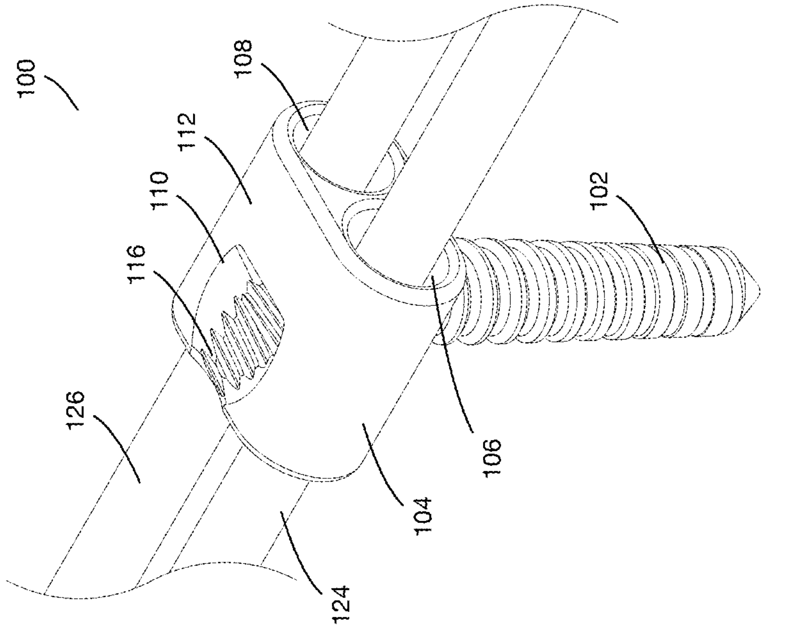
FIG. 2 is a top rear perspective view of the first embodiment of FIG. 1.
Figure 1:
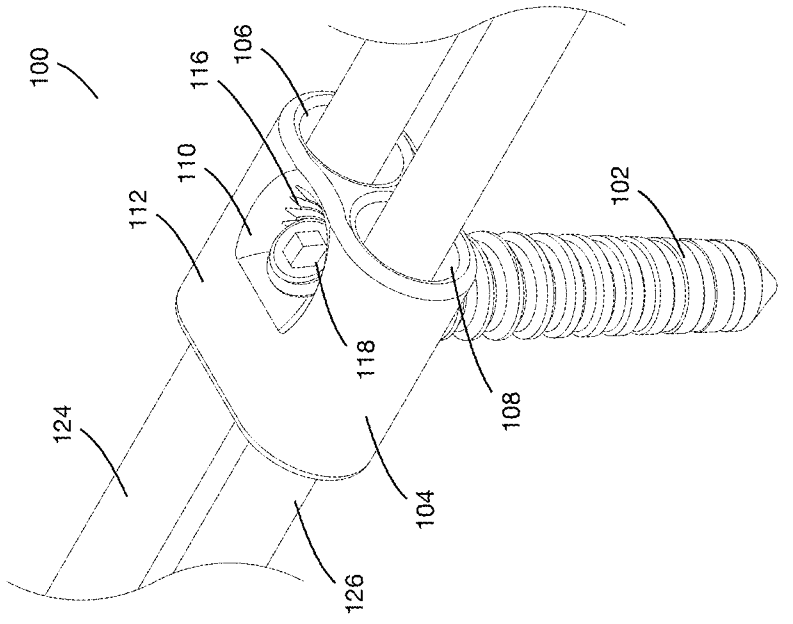
FIG. 1 is a top front perspective view of a first embodiment of the invention in which dual cord channels are provided.
Figure 3:
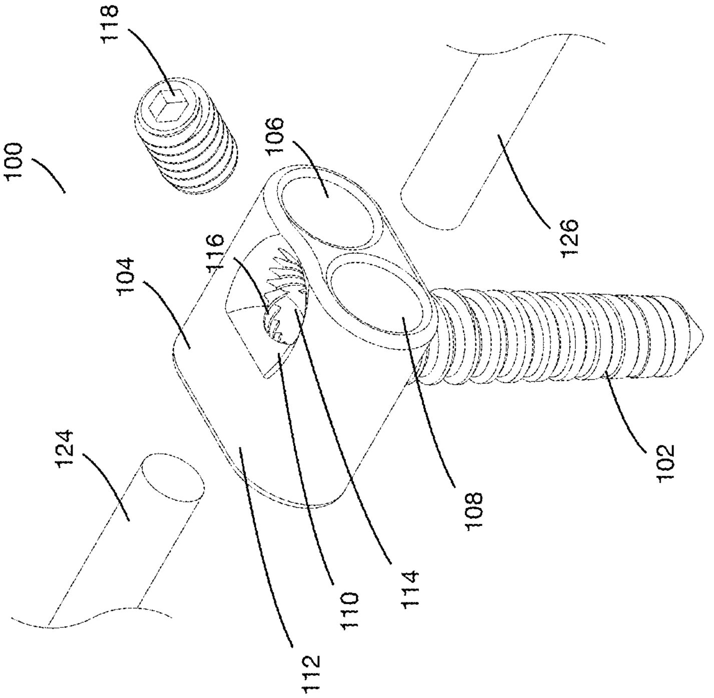
FIG. 3 is an exploded view of the first embodiment of FIG. 1.
Figure 5:
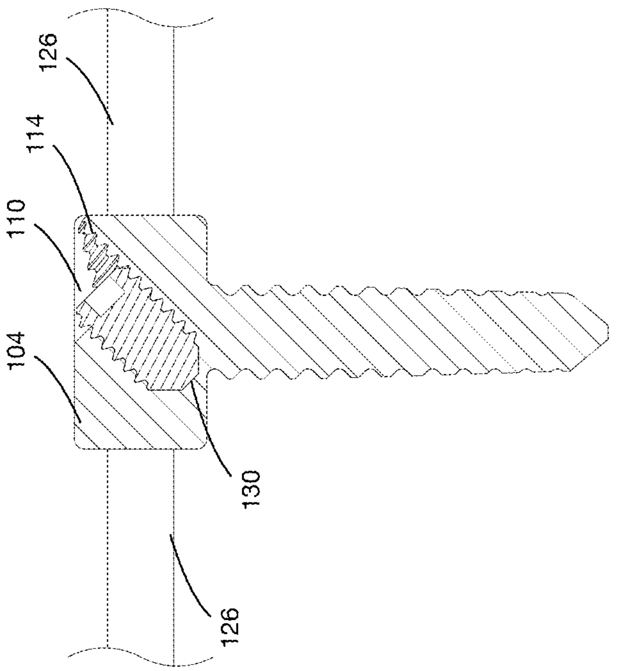
FIG. 5 is a cross-section side view of the first embodiment of FIG. 1.
Figure 4:
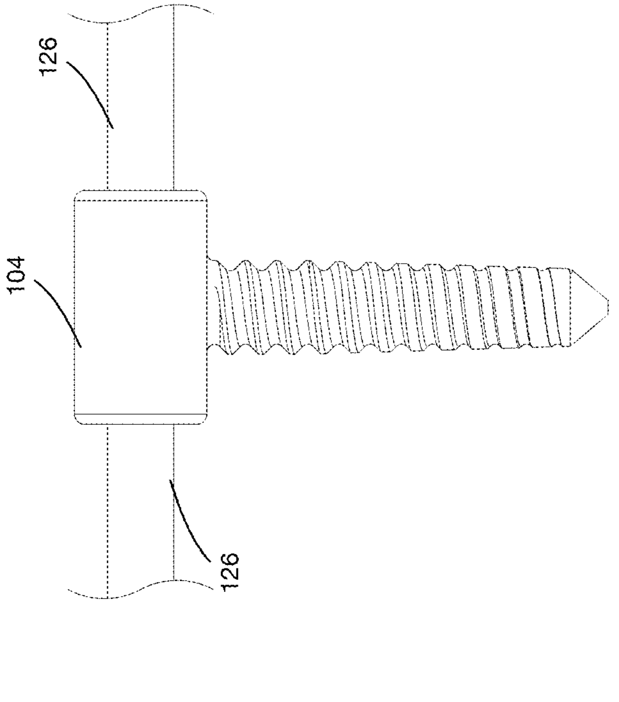
FIG. 4 is a side view of the first embodiment of FIG. 1.
Figure 8:
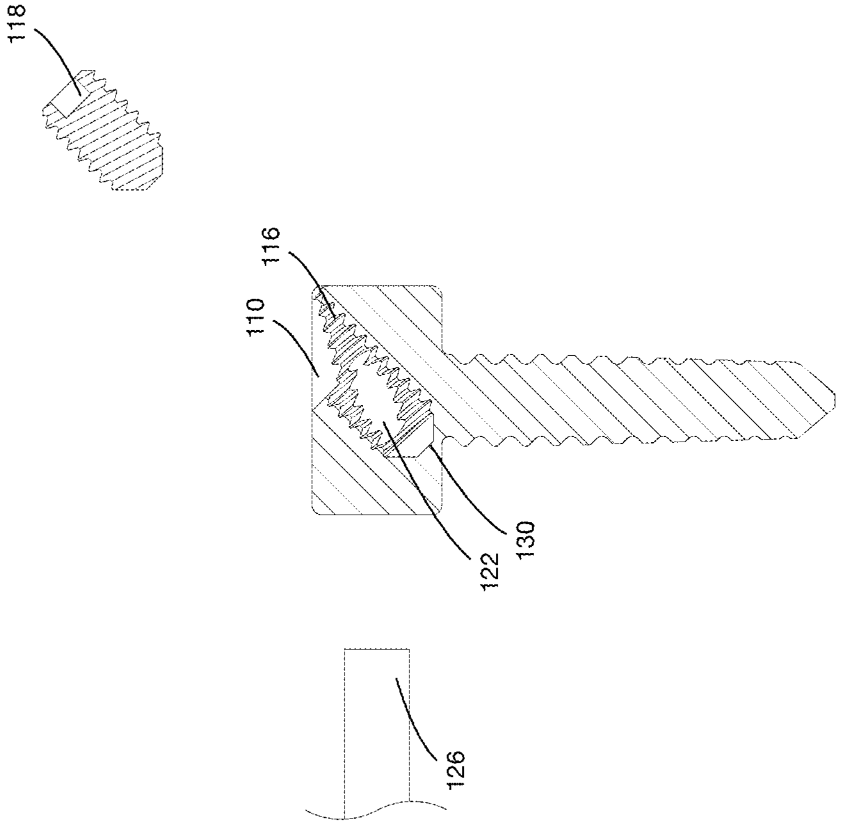
FIG. 8 is a cross-section side view of the first embodiment of FIG. 1 in exploded view format.
Figure 9:
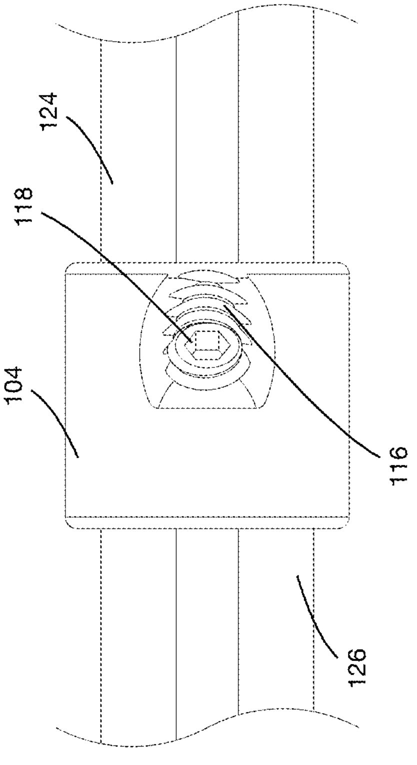
FIG. 9 is a top view of the first embodiment of FIG. 1.

As shown in the cross-section view of FIGS. 5 and 8, a stop 130 is located at the end of the socket 114 against which the threaded fastener is tightened to hold each of the cords within their respective cord channel and to prevent the threaded fastener 118 from being overtightened. The stop 130 as shown is simply the end of the socket 114, but other mechanisms may be used if desired to accomplish the same function.

Figure 25:
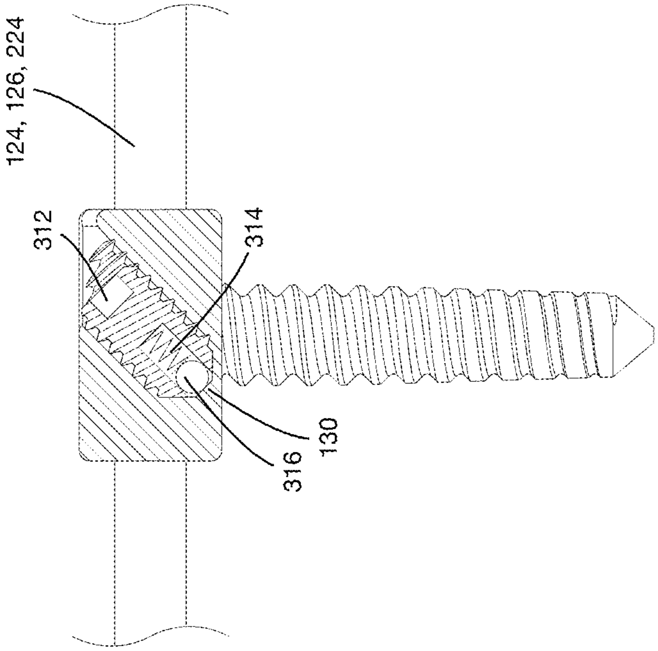
FIG. 25 is a side cross-section view of the first embodiment of FIG. 1 and of the single cord channel of the second embodiment of FIG. 13 showing a ball nose spring plunger comprising a biasing spring within a channel of the fastener adjacent a ball at a distal end of the fastener.

The threaded fastener 118 may optionally include means for biasing the threaded fastener within the socket in order to hold it in place after tightening. As shown in FIG. 25, the means for biasing the threaded fastener within the socket may, for example, be a ball nose spring plunger 312 that has a biasing spring 314 within a channel of the fastener 118 adjacent a ball 316 at a distal end of the fastener. As known in the art, when the threaded fastener 118 is tightened so that the ball 316 is urged against the stop 130, the biasing spring 314 is compressed so as to impart a force in the opposite direction and secure the threaded fastener 118 within the socket 114. Other types of means for biasing may also be used to provide the securing of the fastener 118 within the socket 114, as may be known in the art.

The socket 114 is shown disposed at an acute angle with respect to the top surface 112, in particular a 45-degree angle in the preferred embodiment. This is advantageous since the angled position of the fastener 118 within the socket 114 allows the threads of the fastener 118 to provide a surface against which the cords will abut, thus preventing the cords from being easily removed or otherwise slip out of place. That is, if the threaded fastener were to be inserted at a 0-degree angle with respect to the vertical axis aligned with the post (i.e., straight down into the housing), the threads of the fastener 118 would be essentially parallel to the direction of travel of the cords and fail to adequately hold it in place. Thus, the steeper the angle of the threaded fastener 118 with respect to the vertical axis aligned with the post, the more of a flat surface the threads of the fastener will provide, and the better the cords are held in place by the fastener 118. Although a 90-degree angle would therefore logically provide the greatest holding power, such a steep angle would be impracticable for the surgeon to be able to manipulate the fastener tightening device within the patient's body. Therefore, having the fastener 118 threaded into the socket 114 at an approximately 45-degree angle, the surgeon is provided with ample working space to tighten the fastener while allowing the threads of the fastener a sufficient angle for holding the cord in place.

Figure 26:
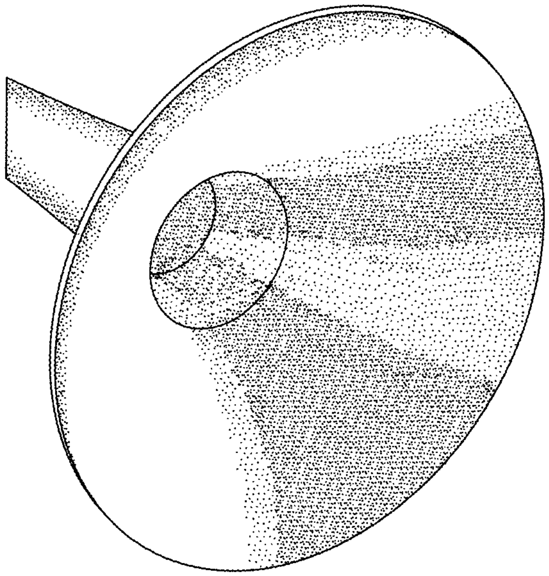
FIG. 26 is illustrative of the bell shape of the flared surfaces.

The cord housing 104 is provided with a flared surface where the cord enters the housing in either direction. The flared surface enables the cord to bend and flex at the entry and exit points without rubbing against a sharp corner edge as in the prior art. This advantageously provides flexibility of the cord without damage or undue wear as in the prior art. The flared surfaces are also provided on the opposite side of the anchor device for maneuverability of the cord at each entry point. Thus, as shown in detail in FIG. 24, each cord channel 106, 108 may have a first end portion 306, a middle portion 308, and a second end portion 310. The first end portion 306 and the second end portion 310 each are outwardly flared, such that the outwardly flared surfaces enable the cord 124, 126 to bend and flex where the cord enters and exits the cord channel without undue wear on the cord. That is, any potential wear on the cord will be minimized by the use of the flared surfaces. FIG. 26 is further illustrative of the shape of the flared surfaces. As can be seen, the flared surface area is similar to that of a bell horn in a trumpet or other brass instrument.

Figure 24:
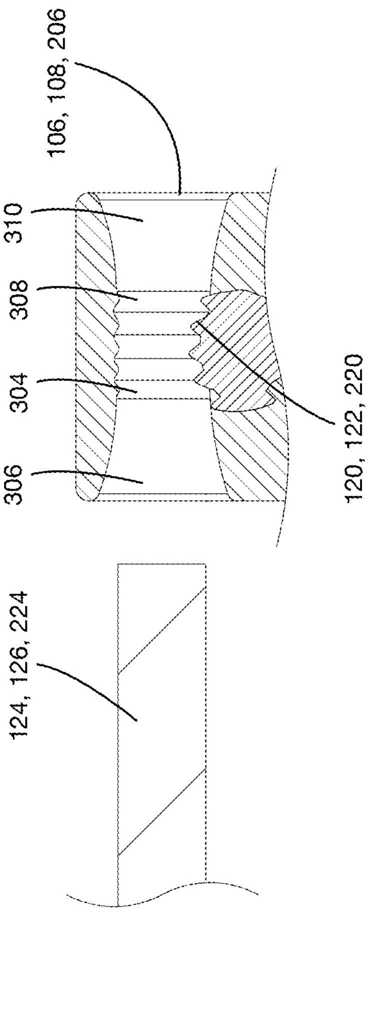
FIG. 24 is a top cross-section view representative of each cord channel of the first embodiment of FIG. 1 and of the single cord channel of the second embodiment of FIG. 13 showing perpendicular ribs within the cord channel.

Also as shown in FIG. 24, the middle portion 308 of each cord channel may have a non-smooth surface suitable for gripping the cord when inserted therewithin. For example, a plurality of ribs 304 may be provided, preferably substantially perpendicular to the direction in which the cord is placed within the channel. As such, a locally compressive force is imparted on the cord so that the cord is held securely in place when the threaded fastener is threaded into the socket, and the cord is prevented from being pulled in either direction in the event there are forces on the cord imparted during use.

Figure 23:
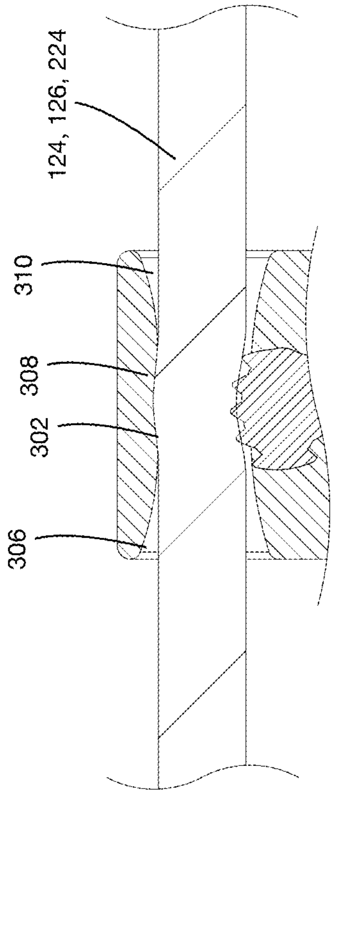
FIG. 23 is a top cross-section view representative of each cord channel of the first embodiment of FIG. 1 and of the single cord channel of the second embodiment of FIG. 13 showing a void within the cord channel.

In an alternative embodiment shown in FIG. 23, a void 302 may be provided along the inside surface of the cord channel 106, 108. In this embodiment, a locally compressive force is imparted on a cord 124, 126 placed within the channel so that the cord at least partially deflects into the void 302 and is held securely in place when the threaded fastener 118 is threaded into the socket 114, and the cord is prevented from being pulled in either direction in the event there are forces on the cord imparted during use. This void 302 may take virtually any shape (e.g. circular, rectangular, etc.) and depth, as long as it is not so deep so as to compromise stability of the anchor device. It also may be beveled so as to provide a smooth transition for the cord, if desired. Additionally, a void may be used in conjunction with the ribs 304 of FIG. 24 to provide additional holding power for the cord.

Alternatively, the non-smooth surface of each cord channel may have a protrusion, whereby a locally compressive force is imparted on a cord placed within the channel so that the cord is held securely in place when a threaded fastener is threaded into the socket, and the cord is prevented from being pulled in either direction in the event there are forces on the cord imparted during use.

With reference to FIGS. 13-22, the second embodiment of the anchor device, which is a single channel anchor device suitable for implementation with a single cord, is shown. The single channel anchor device 200 includes a threaded post 202 suitable for implantation into a bone as known in the art, and a cord housing 204 that is coupled to the post. The cord housing 204 maybe fixedly coupled to the post 202 as shown, so that the connection is rigid and unmoving, or the cord housing may be rotatably or otherwise movably coupled to the post. Shown in FIGS. 11 and 12 is a bone anchoring staple 128, as well known in the art, that may be utilized with the dual channel and single channel anchor devices of the present invention.

In this second embodiment, the cord housing 204 of the single channel anchor device 200 includes a single cord channel 206, which extends through the cord housing 204. The cord channel 206 allows insertion therethrough of a single tensioning cord 224. A cavity 210 is open from a top surface 212 of the cord housing 204, the cavity located adjacent the cord channel 206. The cavity 210 has a socket 214 (see FIG. 15) extending into the housing 204. Preferably, the socket is substantially cylindrical and has socket threads 216 for receiving a threaded fastener 218, which is used to hold the cord 224 in place within the channel 206 after being tensioned by the surgeon. Note that the cord 224 may be inserted or threaded into the cord housing 204 from either direction as may be desired by the surgeon.

Figure 19:
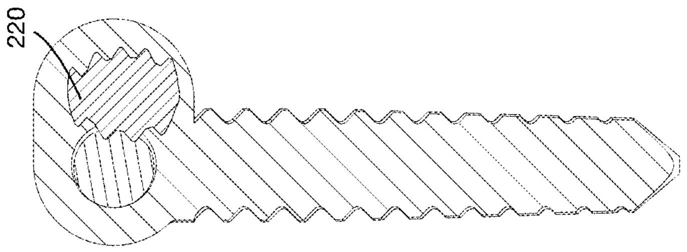
FIG. 19 is a cross-section front view of the second embodiment of FIG. 13.
Figure 18:
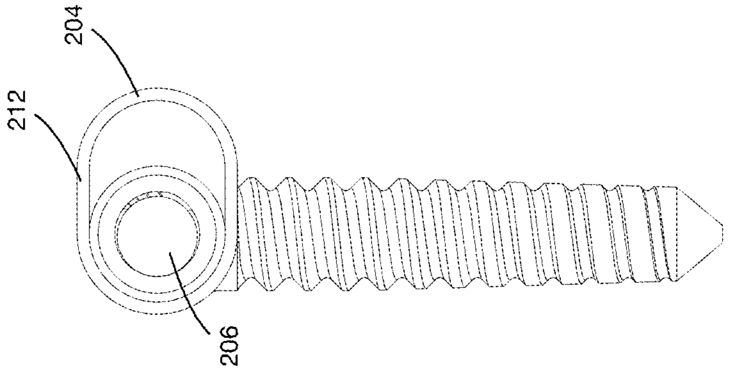
FIG. 18 is a front view of the second embodiment of FIG. 13.
Figure 22:
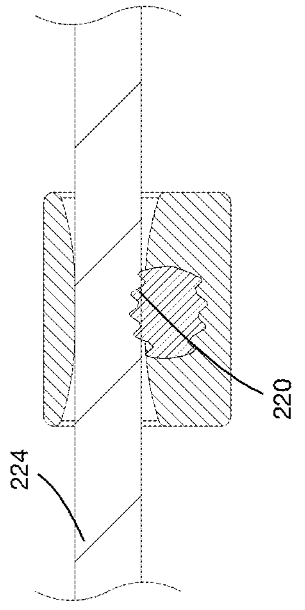
FIG. 22 is a cross-section of the top view of the second embodiment of FIG. 13.

Reference is now made to FIGS. 19 and 22, which show a single socket aperture 220 opening into the cord channel 206. The socket aperture 220 is essentially an opening in the wall of the socket 214 that leads into the cord channel 206. This allows the mating threads of the threaded fastener 218 to enter into the space in the channel 206 and grab the cord 224 that has been inserted therethrough. As the threaded fastener 218 is tightened into the socket 214, the threads of the fastener 218 press against the cord 224 in order to secure the cord within the channel 206. See also FIG. 21.

As such, when the cord 224 is inserted through the cord channel 206 and the threaded fastener 218 is threaded into the socket 214, the threaded fastener 218 protrudes into the socket aperture 220 to at least partially compress the cord 224 and to hold the cord within the cord channel 206.

It is noted that in the prior art, it is the tip of the fastener (such as a set screw) which impinges directly upon the cord in place within the corresponding anchor device. However, this invention does not rely on the tip of the fastener 218 to secure the cord in place, i.e. the tip of the fastener does not impinge directly on and impart direct force upon the cord. Instead, the fastener 218 is threaded within the socket threads 216 of the socket 214 such that the threads of the fastener 218 enter into the space in the channel 206 and grab the cord 224 that has been inserted therethrough.

As shown, in the preferred embodiments, the head of the fastener 218 is countersunk within the cavity 210 of the housing 204, although this is not required. The head of the fastener 218 is shown with a hex profile, but others may be used, such as square, slotted, Phillips, etc. This avoids the problem in the prior art described above wherein the force of the tip of the set screw directly onto the cord will deleteriously pinch the cord, which can lead to undesired fraying or other damage to the cord.

Optionally, the threads of the threaded fastener have sharp crested threads near a tip of the fastener, rounded crested threads in a middle portion of the fastener, and sharp crested threads near a head of the fastener. By implementing rounded crested threads rather than sharp crested threads in the middle portion of the fastener, the cord will not be undesirably cut by the threads of the fastener as the hold the cord securely in place.

Figure 17:
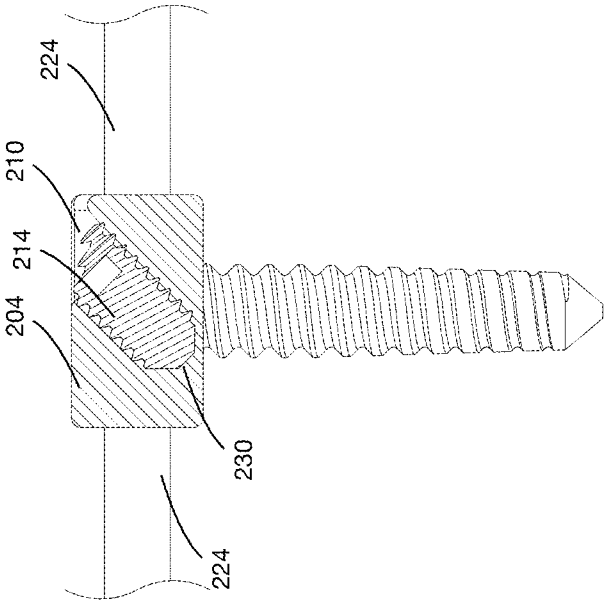
FIG. 17 is a cross-section side view of the second embodiment of FIG. 13.
Figure 16:
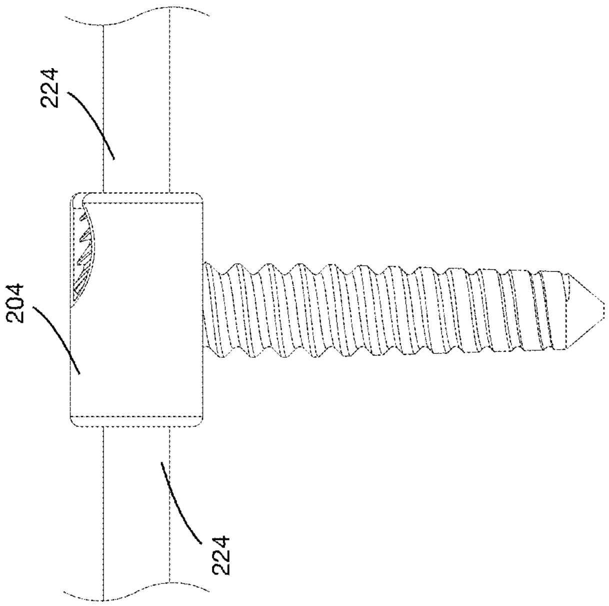
FIG. 16 is a side view of the second embodiment of FIG. 13.
Figure 20:
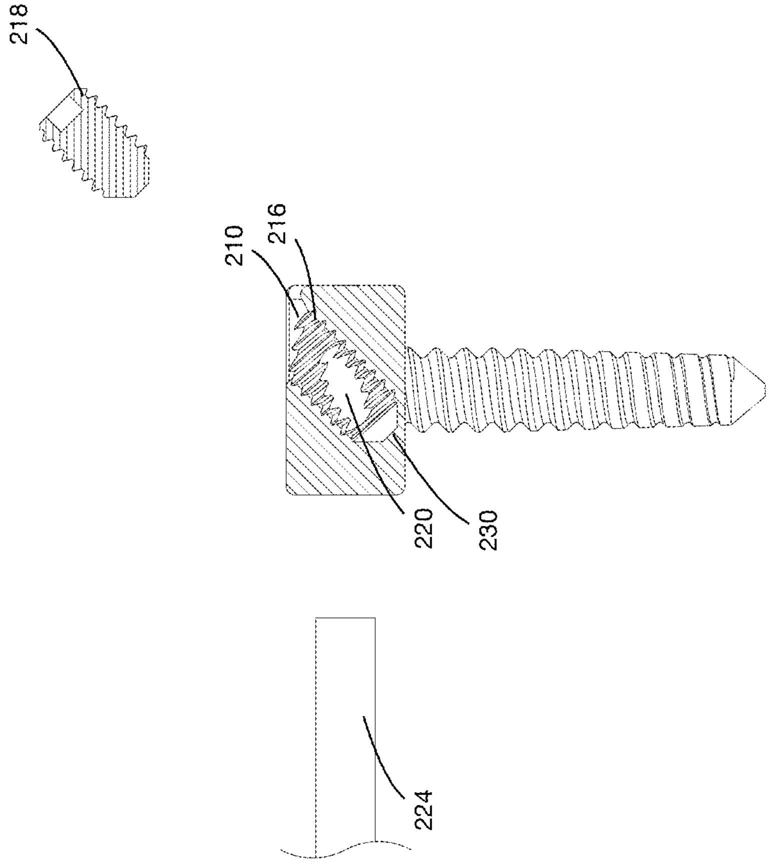
FIG. 20 is a cross-section side view of the second embodiment of FIG. 13 in exploded view format.
Figure 21:
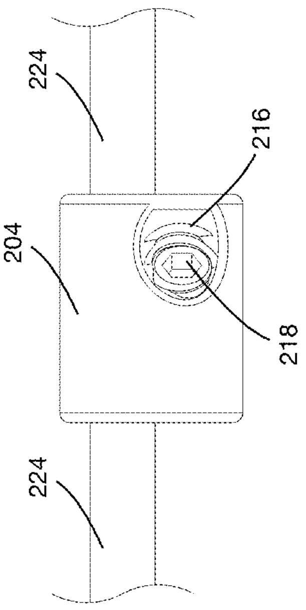
FIG. 21 is a top view of the second embodiment of FIG. 13.

As shown in the cross-section view of FIGS. 17 and 20, a stop 230 is located at the end of the socket 214 against which the threaded fastener 218 is tightened to hold the cord 224 within the cord channel 206 and to prevent the threaded fastener 218 from being overtightened. The stop 230 as shown is simply the end of the socket 214, but other mechanisms may be used if desired to accomplish the same function.

The threaded fastener 218 may optionally include means for biasing the threaded fastener within the socket in order to hold it in place after tightening. As shown in FIG. 25, the means for biasing the threaded fastener within the socket may, for example, be a ball nose spring plunger 312 that has a biasing spring 314 within a channel of the fastener adjacent a ball 316 at a distal end of the fastener. As known in the art, when the threaded fastener is tightened so that the ball 316 is urged against the stop 230, the biasing spring 314 is compressed so as to impart a force in the opposite direction and secure the threaded fastener 218 within the socket 214. Other types of means for biasing may also be used to provide the securing of the fastener 218 within the socket 214, as may be known in the art.

The socket 214 is shown disposed at an acute angle with respect to the top surface 212, in particular a 45-degree angle in the preferred embodiment. This is advantageous since the angled position of the fastener 218 within the socket 214 allows the threads of the fastener 218 to provide a surface against which the cord will abut, thus preventing the cord from being easily removed or otherwise slip out of place. That is, if the threaded fastener were to be inserted at a 0-degree angle with respect to the vertical axis aligned with the post (i.e., straight down into the housing), the threads of the fastener 218 would be essentially parallel to the direction of travel of the cord and fail to adequately hold it in place. Thus, the steeper the angle of the threaded fastener 218 with respect to the vertical axis alligned with the post, the more of a flat surface the threads of the fastener will provide, and the better the cord is held in place by the fastener 218. Although a 90-degree angle would therefore logically provide the greatest holding power, such a steep angle would be impracticable for the surgeon to be able to manipulate the fastener tightening device within the patient's body. Therefore, having the fastener 218 threaded into the socket 214 at an approximately 45-degree angle, the surgeon is provided with ample working space to tighten the fastener while allowing the threads of the fastener a sufficient angle for holding the cord in place.

The cord housing 204 is provided with a flared surface where the cord enters the housing in either direction. The flared surface enables the cord to bend and flex at the entry and exit points without rubbing against a sharp corner edge as in the prior art. This advantageously provides flexibility of the cord without damage or undue wear as in the prior art. The flared surfaces are also provided on the opposite side of the anchor device for maneuverability of the cord at each entry point. Thus, as shown in detail in FIG. 24, the cord channel 206 may have a first end portion 306, a middle portion 308, and a second end portion 310. The first end portion 306 and the second end portion 310 each are outwardly flared, such that the outwardly flared surfaces enable the cord 224 to bend and flex where the cord enters and exits the cord channel without undue wear on the cord. That is, any potential wear on the cord will be minimized by the use of the flared surfaces. FIG. 26 is further illustrative of the shape of the flared surfaces. As can be seen, the flared surface area is similar to that of a bell horn in a trumpet or other brass instrument.

Also as shown in FIG. 24, the middle portion 308 of each cord channel may have a non-smooth surface suitable for gripping the cord when inserted therewithin. For example, a plurality of ribs 304 may be provided, preferably substantially perpendicular to the direction in which the cord is placed within the channel. As such, a locally compressive force is imparted on the cord so that the cord is held securely in place when the threaded fastener is threaded into the socket, and the cord is prevented from being pulled in either direction in the event there are forces on the cord imparted during use.

In an alternative embodiment shown in FIG. 23, a void 302 may be provided along the inside surface of the cord channel 206. In this embodiment, a locally compressive force is imparted on a cord 224 placed within the channel so that the cord at least partially deflects into the void 302 and is held securely in place when the threaded fastener 218 is threaded into the socket 214, and the cord is prevented from being pulled in either direction in the event there are forces on the cord imparted during use. This void 302 may take virtually any shape (e.g. circular, rectangular, etc.) and depth, as long as it is not so deep so as to compromise stability of the anchor device. It also may be beveled so as to provide a smooth transition for the cord, if desired. Additionally, a void may be used in conjunction with the ribs 304 of FIG. 24 to provide additional holding power for the cord.

Alternatively, the non-smooth surface of each cord channel may have a protrusion, whereby a locally compressive force is imparted on a cord placed within the channel so that the cord is held securely in place when a threaded fastener is threaded into the socket, and the cord is prevented from being pulled in either direction in the event there are forces on the cord imparted during use.

We claim:

1. An anchor device for insertion into a bone, comprising:
- a post suitable for implantation into a bone, and
- a cord housing coupled to the post, comprising:
  - a pair of cord channels comprising a first cord channel extending through the housing and a second cord channel extending through the housing:
  - a cavity open from a top surface of the housing, the cavity comprising a socket extending into the housing, the socket comprising:
    - socket threads for receiving a threaded fastener,
    - a first socket aperture opening into the first cord channel, and a second socket aperture opening into the second cord channel;

the socket threads disposed to allow a threaded fastener, comprising fastener threads, to be threaded into the socket and protrude into the first socket aperture to enter the first cord channel such that the fastener threads press against a first cord inserted through the first cord channel and at least partially compress the first cord against an opposing inner wall of the first cord channel, and protrude into the second socket aperture to enter the second cord channel such that the fastener threads press against a second cord inserted through the second cord channel and at least partially compress the second cord against an opposing inner wall of the second cord channel, and hold each of the cords within their respective cord channel, further comprising a threaded fastener comprising fastener threads mated to the socket threads, wherein the threads of the threaded fastener comprise sharp crested threads near a tip of the fastener, rounded crested threads in a middle portion of the fastener, and sharp crested threads near a head of the fastener.

2. An anchor device for insertion into a bone, comprising:

a post suitable for implantation into a bone, and a cord housing coupled to the post, comprising:

a pair of cord channels comprising a first cord channel extending through the housing and a second cord channel extending through the housing;

a cavity open from a top surface of the housing, the cavity comprising a socket extending into the housing, the socket comprising:

socket threads for receiving a threaded fastener, a first socket aperture opening into the first cord channel, and a second socket aperture opening into the second cord channel;

the socket threads disposed to allow a threaded fastener, comprising fastener threads, to be threaded into the socket and protrude into the first socket aperture to enter the first cord channel such that the fastener threads press against a first cord inserted through the first cord channel and at least partially compress the first cord against an opposing inner wall of the first cord channel, and protrude into the second socket aperture to enter the second cord channel such that the fastener threads press against a second cord inserted through the second cord channel and at least partially compress the second cord against an opposing inner wall of the second cord channel, and hold each of the cords within their respective cord channel, further comprising a threaded fastener comprising fastener threads mated to the socket threads, wherein the socket terminates at a stop against which the threaded fastener is tightened to hold each of the cords within their respective cord channel, wherein the threaded fastener comprises means for biasing the threaded fastener within the socket.

3. The anchor device of claim 2 wherein the means for biasing the threaded fastener within the socket comprises a ball nose spring plunger comprising a biasing spring within a channel of the fastener adjacent a ball at a distal end of the fastener;

whereby, when the threaded fastener is tightened so that the ball is urged against the stop, the biasing spring is compressed so as to impart a force in the opposite direction and secure the threaded fastener within the socket.

4. An anchor device for insertion into a bone, comprising:

a post suitable for implantation into a bone, and a cord housing coupled to the post, comprising:

a pair of cord channels comprising a first cord channel extending through the housing and a second cord channel extending through the housing;

a cavity open from a top surface of the housing, the cavity comprising a socket extending into the housing, the socket comprising:

socket threads for receiving a threaded fastener, a first socket aperture opening into the first cord channel, and a second socket aperture opening into the second cord channel;

the socket threads disposed to allow a threaded fastener, comprising fastener threads, to be threaded into the socket and protrude into the first socket aperture to enter the first cord channel such that the fastener threads press against a first cord inserted through the first cord channel and at least partially compress the first cord against an opposing inner wall of the first cord channel, and protrude into the second socket aperture to enter the second cord channel such that the fastener threads press against a second cord inserted through the second cord channel and at least partially compress the second cord against an opposing inner wall of the second cord channel, and hold each of the cords within their respective cord channel;

wherein the cavity is located between the pair of cord channels and wherein the socket is disposed at an acute angle with respect to the top surface of the housing.

5. The anchor device of claim 4, wherein the acute angle is 45 degrees.

6. The anchor device of claim 4 wherein each cord channel comprises a first end portion, a middle portion, and a second end portion, wherein the first end portion and the second end portion comprise surfaces that are outwardly flared, whereby the outwardly flared surfaces enable the cord to bend and flex where the cord enters and exits the cord channel without undue wear on the cord.

7. The anchor device of claim 6 wherein the middle portion of each cord channel comprises a non-smooth surface suitable for gripping the cord when inserted therewithin.

8. The anchor device of claim 7 wherein the non-smooth surface of each cord channel comprises a plurality of ribs extending substantially perpendicular to the direction in which the cord is placed within the channel, whereby a locally compressive force is imparted on the cord so that the cord is held securely in place when a threaded fastener is threaded into the socket, and the cord is prevented from being pulled in either direction in the event there are forces on the cord imparted during use.

9. The anchor device of claim 7 wherein the non-smooth surface of each cord channel comprises a void, whereby a locally compressive force is imparted on a cord placed within the channel so that the cord at least partially deflects into the void and is held securely in place when a threaded fastener is threaded into the socket, and the cord is prevented from being pulled in either direction in the event there are forces on the cord imparted during use.

10. The anchor device of claim 7 wherein the non-smooth surface of each cord channel comprises a protrusion;

whereby a locally compressive force is imparted on a cord placed within the channel so that the cord is held securely in place when a threaded fastener is threaded into the socket, and the cord is prevented from being pulled in either direction in the event there are forces on the cord imparted during use.

11. The anchor device of claim 4 wherein the cord housing is fixedly coupled to the post.

12. The anchor device of claim 4 wherein the threaded fastener holds each of the cords within their respective cord channel without a bottom tip surface of the threaded fastener impinging on the cords.

13. An anchor device for insertion into a bone, comprising:

a post suitable for implantation into a bone, and a cord housing coupled to the post, comprising:

a cord channel extending through the housing, a cavity open from a top surface of the housing, the cavity located adjacent the cord channel, the cavity comprising a socket extending into the housing, the socket comprising:

socket threads for receiving a threaded fastener, and a socket aperture opening into the cord channel;

the socket threads disposed to allow a threaded fastener, comprising fastener threads, to be threaded into the socket and protrude into the socket aperture to enter the cord channel such that the fastener threads press against a cord inserted through the cord channel and at least partially compress the cord against an opposing inner wall of the cord channel, and hold the cord within the cord channel;

further comprising a threaded fastener comprising fastener threads mated to the socket threads, wherein the threads of the threaded fastener comprise sharp crested threads near a tip of the fastener, rounded crested threads in a middle portion of the fastener, and sharp crested threads near a head of the fastener.

14. An anchor device for insertion into a bone, comprising:

a post suitable for implantation into a bone, and a cord housing coupled to the post, comprising:

a cord channel extending through the housing, a cavity open from a top surface of the housing, the cavity located adjacent the cord channel, the cavity comprising a socket extending into the housing, the socket comprising:

socket threads for receiving a threaded fastener, and a socket aperture opening into the cord channel;

the socket threads disposed to allow a threaded fastener, comprising fastener threads, to be threaded into the socket and protrude into the socket aperture to enter the cord channel such that the fastener threads press against a cord inserted through the cord channel and at least partially compress the cord against an opposing inner wall of the cord channel, and hold the cord within the cord channel;

further comprising a threaded fastener comprising fastener threads mated to the socket threads, wherein the threaded fastener comprises means for biasing the threaded fastener within the socket.

15. The anchor device of claim 14 wherein the means for biasing the threaded fastener within the socket comprises a ball nose spring plunger comprising a biasing spring within a channel of the fastener adjacent a ball at a distal end of the fastener;

whereby, when the threaded fastener is tightened so that the ball is urged against the stop, the biasing spring is compressed so as to impart a force in the opposite direction and secure the threaded fastener within the socket.

16. An anchor device for insertion into a bone, comprising:

a post suitable for implantation into a bone, and a cord housing coupled to the post, comprising:

a cord channel extending through the housing, a cavity open from a top surface of the housing, the cavity located adjacent the cord channel, the cavity comprising a socket extending into the housing, the socket comprising:

socket threads for receiving a threaded fastener, and a socket aperture opening into the cord channel;

the socket threads disposed to allow a threaded fastener, comprising fastener threads, to be threaded into the socket and protrude into the socket aperture to enter the cord channel such that the fastener threads press against a cord inserted through the cord channel and at least partially compress the cord against an opposing inner wall of the cord channel, and hold the cord within the cord channel, wherein the cord channel is located directly over the post, wherein the socket is disposed at an acute angle with respect to the top surface of the housing.

17. The anchor device of claim 16, wherein the acute angle is 45 degrees.

18. The anchor device of claim 16 wherein the cord channel comprises a first end portion, a middle portion, and a second end portion, wherein the first end portion and the second end portion comprise surfaces that are outwardly flared, whereby the outwardly flared surfaces enable the cord to bend and flex where the cord enters and exits the cord channel without undue wear on the cord.

19. The anchor device of claim 18 wherein the middle portion of the cord channel comprises a non-smooth surface suitable for gripping the cord when inserted therewithin.

20. The anchor device of claim 19 wherein the non-smooth surface of the cord channel comprises a plurality of ribs extending substantially perpendicular to the direction in which the cord is placed within the channel, whereby a locally compressive force is imparted on the cord so that the cord is held securely in place when a threaded fastener is threaded into the socket, and the cord is prevented from being pulled in either direction in the event there are forces on the cord imparted during use.

21. The anchor device of claim 19 wherein the non-smooth surface of the cord channel comprises a void, whereby a locally compressive force is imparted on a cord placed within the channel so that the cord at least partially deflects into the void and is held securely in place when a threaded fastener is threaded into the socket, and the cord is prevented from being pulled in either direction in the event there are forces on the cord imparted during use.

22. The anchor device of claim 19 wherein the non-smooth surface of each cord channel comprises a protrusion; whereby a locally compressive force is imparted on a cord placed within the channel so that the cord is held securely in place when a threaded fastener is threaded into the socket, and the cord is prevented from being pulled in either direction in the event there are forces on the cord imparted during use.

23. The anchor device of claim 16 wherein the cord housing is fixedly coupled to the post.

24. The anchor device of claim 16 wherein the threaded fastener holds the cord within the cord channel without a bottom tip surface of the threaded fastener impinging on the cord.

* * * * *